United States Patent [19]

Steacy

[11] Patent Number: 4,761,513

[45] Date of Patent: Aug. 2, 1988

[54] TEMPERATURE CONTROL FOR AROMATIC ALKYLATION PROCESS

[75] Inventor: Paul C. Steacy, Mount Prospect, Ill.

[73] Assignee: UOP Inc., Des Plaines, Ill.

[21] Appl. No.: 68,520

[22] Filed: Jul. 1, 1987

[51] Int. Cl.$^4$ ............................................... C07C 2/68
[52] U.S. Cl. .................................................... 585/467
[58] Field of Search .......................................... 585/467

[56] References Cited

U.S. PATENT DOCUMENTS

| | | | |
|---|---|---|---|
| 3,007,983 | 11/1961 | Clauson | 260/683.46 |
| 3,489,818 | 1/1970 | Hervert | 260/671 |
| 3,751,504 | 8/1973 | Keown et al. | 260/672 T |
| 4,283,306 | 8/1981 | Herkes | 252/432 |
| 4,444,989 | 4/1984 | Herkes | 585/467 |
| 4,490,570 | 12/1984 | Forward et al. | 585/467 |

*Primary Examiner*—Curtis R. Davis
*Attorney, Agent, or Firm*—Thomas K. McBride; John G. Tolomei

[57] ABSTRACT

The quench system for a toluene methylation process is improved by using the methylating agent as a quench medium that is introduced between sequential reaction zones. A stream of toluene and any resulting alkylate product is passed sequentially through the reaction zones while the methylating agent in vapor or liquid form or a combinations thereof is added at points intermediate any two reaction zones. The proportion of vapor phase and liquid phase methanol is adjusted to control the enthalpy of the methylating agent and provide temperature reduction by the vaporization of the liquid component of the methylating agent. The control system for the methylating agent varies the total amount of methanol in the relative proportions of liquid and vapor phase in response to temperature and composition parameters measured at the inlet to any reaction zone. This arrangement is particularly beneficial where the methylating agent is corrosive and steam is used to inhibit the corrosive effects. A particular arrangement of this invention allows the steam to be added only as needed so that a minimum steam concentration can be maintained.

13 Claims, 2 Drawing Sheets

TEMPERATURE CONTROL FOR AROMATIC ALKYLATION PROCESS

FIELD OF THE INVENTION

This invention relates broadly to the alkylation of aromatic hydrocarbons. More specifically, this invention relates to a method for controlling temperatures in a multistage reaction process for the alkylation of aromatic hydrocarbons.

BACKGROUND OF THE INVENTION

Processes for the alkylation of aromatic hydrocarbons are well known. Such processes typically utilize an aromatic reactant such as benzene or toluene which is reacted over a solid catalyst with an aliphatic alkylating agent that contains a straight chain paraffin moiety such as a methyl or ethyl group which can be in such forms as a paraffin, an alcohol, or a chloride. The process of alkylating aromatic hydrocarbons, or alkylation in general, involves the evolution of large amounts of heat. As a result, it is commonplace for an alkylation process to incorporate means for cooling the reaction zone or reactants in an alkylation process. Obtaining maximum performance in a multiple reaction zone process for the alkylation of aromatic hydrocarbons places a number of demands on the composition and properties of suitable quench medium. First, certain quench mediums such as liquid water or steam are unacceptable for many aromatic alkylation processes since it is known that liquid water, and in many cases steam, can permanently deactivate the catalyst by dealumination of catalyst supports or other destructive reactions. Water or steam can also pose other problems with zeolitic catalyst supports unless special precautions are taken to protect the zeolite matrix from unwanted cations such as sodium. In addition, when a series of reaction zones are used to alkylate aromatic hydrocarbons, deactivation of the catalyst will usually occur at different rates in the different reaction zones. Therefore, wide variations in the quench requirements exist for the different reaction zones. As a result, whatever quench medium is used, it must have sufficient heat capacity to effect the desired temperature control in each reaction zone. Therefore, regardless of the composition of the quench, the heat capacity of the quench is normally a fixed variable in the operation of an exothermic process and the volume of the quench is varied to obtain the desired degree of cooling. This is normally the case whether the heat capacity of the quench is based on the specific heat of the quench material alone or also includes a phase change for additional heat absorption. In order to be sure that adequate quench capacity is available, a quench stream is selected that can be added to a reaction zone in sufficient quantity. Whenever a quench medium is added to a reaction zone in a quantity greater than that required for the reaction occurring therein, it imposes additional cost to the process in the form of separation facilities and utilities.

INFORMATION DISCLOSURE

An example of a representative aromatic alkylation process is shown in U.S. Pat. No. 4,283,306 where toluene is passed over a crystalline silicate catalyst to react with a methylating agent such as methanol, dimethylether, methylchloride, or methylbromide to mention just a few possible compounds.

A similar process for methylating toluene is taught in U.S. Pat. No. 4,444,989 where toluene and a methylating agent are passed over a promoted or unpromoted crystalline silicate catalyst for the production of para-xylene. The '989 patent teaches passage of the toluene reagent through a series of reaction zones, and the addition of methylating agent to each reaction zone in a relatively small volume so that the total concentration of methylating agent in each reaction zone remains low thereby shifting the reaction equilibrium toward the production of para-xylene and preventing the formation of unwanted substituted aromatics.

Another process for the alkylation of toluene with an alkyl substituent is taught in U.S. Pat. No. 4,490,570 which uses a silicalite catalyst to preferentially obtain para-isomers. The '570 patent also mentions that a steam co-feed can be used with the hydrocarbon reactants to enhance performance of the process. Although the '570 patent does not describe the benefits that can be obtained by the use of a steam co-feed, it is known that for corrosive methylating agents the use of steam can preserve metal surfaces subject to corrosive attack, by keeping the metal in an oxidized state to resist the corrosive effects of methanol and other corrosive alkylating agents.

U.S. Pat. No. 3,007,983 teaches the use of self-refrigeration in the alkylation of aliphatic hydrocarbons by the evaporation of one of the reactants.

Again, self-refrigeration in the alkylation of aromatic hydrocarbons is taught in U.S. Pat. No. 3,489,818 wherein one of the reactant streams is at least partially vaporized in the reaction zone to use the latent heat of vaporization as a means of absorbing heat and reducing reaction zone temperatures.

Staged addition of the aromatic reactant as a quench medium into a series of reaction zones is taught in U.S. Pat. No. 3,751,504. In the '504 patent, liquid alkyl reactants are added to quench some of the reaction zones as unreacted aromatics reactants and accumulated products progress through the series of reaction zones.

BRIEF SUMMARY OF THE INVENTION

Accordingly, it is an object of this invention to provide a quench system for alkylating aromatic hydrocarbons in a series of reaction zones.

It is a further object of this invention to provide a quench system that will not require additional separation facilities or the addition of unwanted compounds into the reaction zones.

It is a further object of this invention to provide a quench system that will minimize the introduction of steam co-feed into a series of reaction zones for alkylating aromatic hydrocarbons.

It has been discovered that the alkylating reactant added in small quantities through a series of reaction zones for alkylating aromatic hydrocarbons can be divided into liquid and vapor phase streams which are proportionately added to the intermediate inlets of reaction zones and completely fulfill the quenching requirements for the process. This process is particularly beneficial in those cases where steam is desired to minimize the corrosive effects of a vapor phase alkylating agent.

Accordingly, in one embodiment, this invention is an improved process for alkylating aromatic hydrocarbons in a series of exothermic reaction zones. The type of process improved by this invention passes the aromatic hydrocarbon serially through the reaction zones and adds a separate stream of alkylating agent to the inlet of each reaction zone. In each reaction zone, the aromatic hydrocarbon and alkylation agent contact an alkylation catalyst at alkylation conditions with the alkylation product and any unreacted aromatic hydrocarbon or alkylating agent passing from the first reaction zone through the remaining reaction zones in the series. Alkylate product is recovered from the last reaction zone. The improvement of this invention is in the use of vapor phase alkylating agent and liquid phase alkylating agent to control temperatures in the reaction zones. These different phase streams are combined to make up at least one of the separate streams of alkylating agent entering one of the series of reaction zones and at the same time provide a quench stream to that reaction zone. The relative proportion of liquid and vapor phase alkylating agent making up the quench and alkylation stream is controlled to provide a predetermined degree of quenching.

A more limited aspect of this invention deals with the addition of steam to the quenching medium in varying proportions. Where it is desired to keep a fixed proportion of steam in a vapor phase of the alkylation medium, the quench system of this invention facilitates the introduction of steam at no more than the required proportion in those sections of the process equipment where a minimum concentration of steam is required. The ability to maintain the steam concentration in no more than the desired amount improves catalyst life and activity in those operations where steam is known to have a deleterious effect on catalyst.

Other objects, embodiments, and advantages of this invention are set forth in the following detailed description.

BRIEF DESCRIPTION OF THE DRAWING

The drawing shows a schematic flow diagram for the methylation of toluene using methanol as a methylating agent. The methylation is carried out in a series of reaction zones 7-11 wherein the reaction zones have varying degrees of catalyst deactivation. Methanol enters the process through a pipeline 1 which splits into a header line 2, for delivering liquid methanol to the reaction zones and a pipeline 3 that ends at a quench heater 4. Vapor methanol leaves the heater through header line 5 which supplies vapor methanol to reaction zones 7-11 through branch lines 12-17, respectively. Liquid methanol from line 2 can be introduced into reaction zones 7-11 through a series of branch lines 18-22 that connect header line 2 with branch lines 12-17, respectively. At its end, header line 2 intersects toluene feed line 24 to combine liquid methanol with the toluene feed entering the process. A steam header line 26 supplies steam to the process through a series of branch connections. Branch connection 30 introduces steam into line 3. Branch connections 32-36 can introduce steam into branch lines 12-17, respectively, ahead of the point of liquid methanol introduction. The end of header line 26 joins toluene feed line 24 to combine steam with the toluene feed and liquid methanol. The combined steam, methanol, and toluene stream pass through a heat exchanger 38, flow through a line 39 to heater 40 and finally to the inlet of reactor 6. Toluene, steam and reaction products flow serially through reactors 6-11 as additional steam and methanol are added at points intermediate the reaction zones. Pipeline 42 receives the methylation product from reactor 11. The contents of line 42 pass through exchanger 38 to heat the feed components in feed line 24.

DETAILED DESCRIPTION OF THE PREFERRED EMBODIMENTS

Figure 1A:
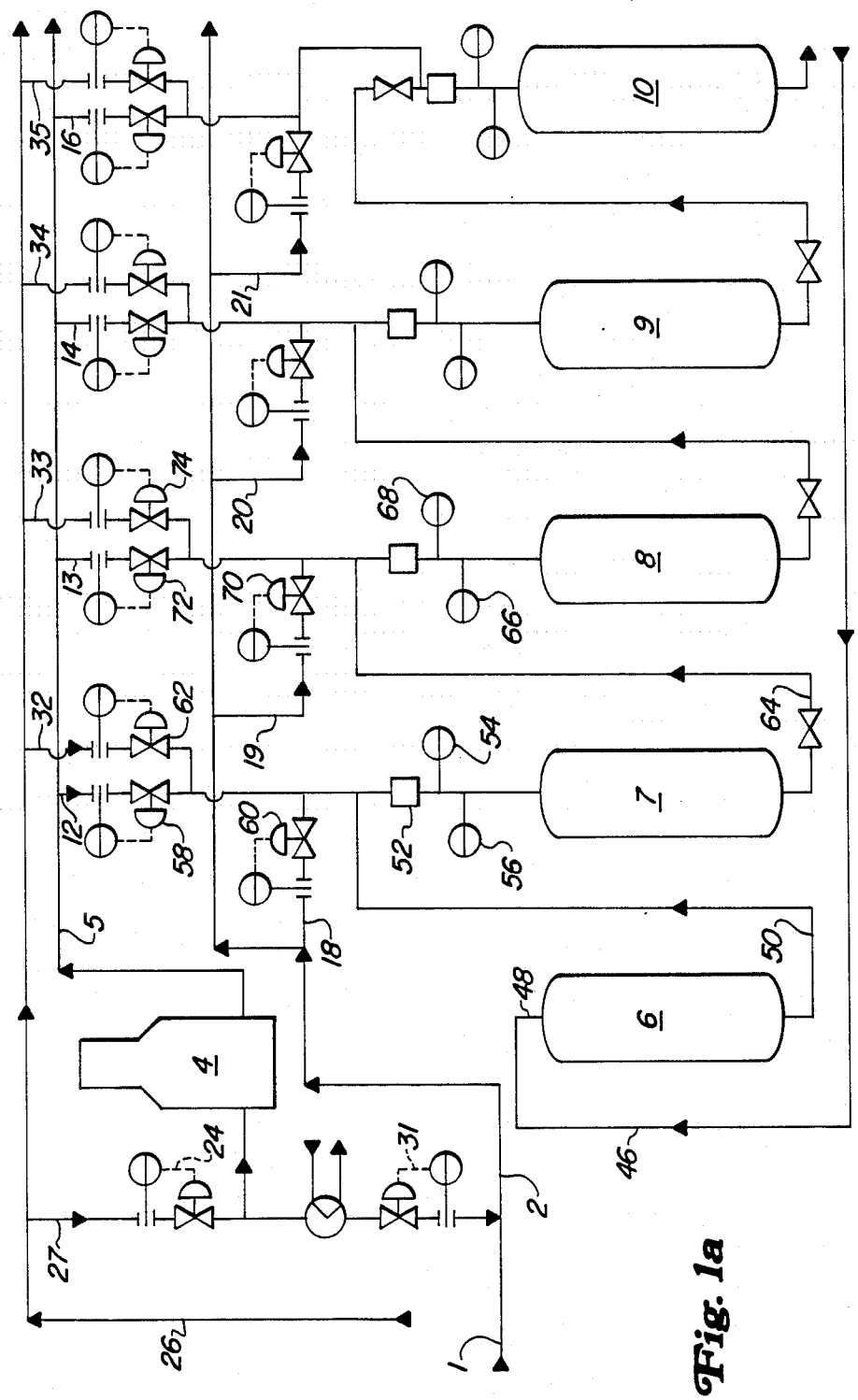
Figure 1B:
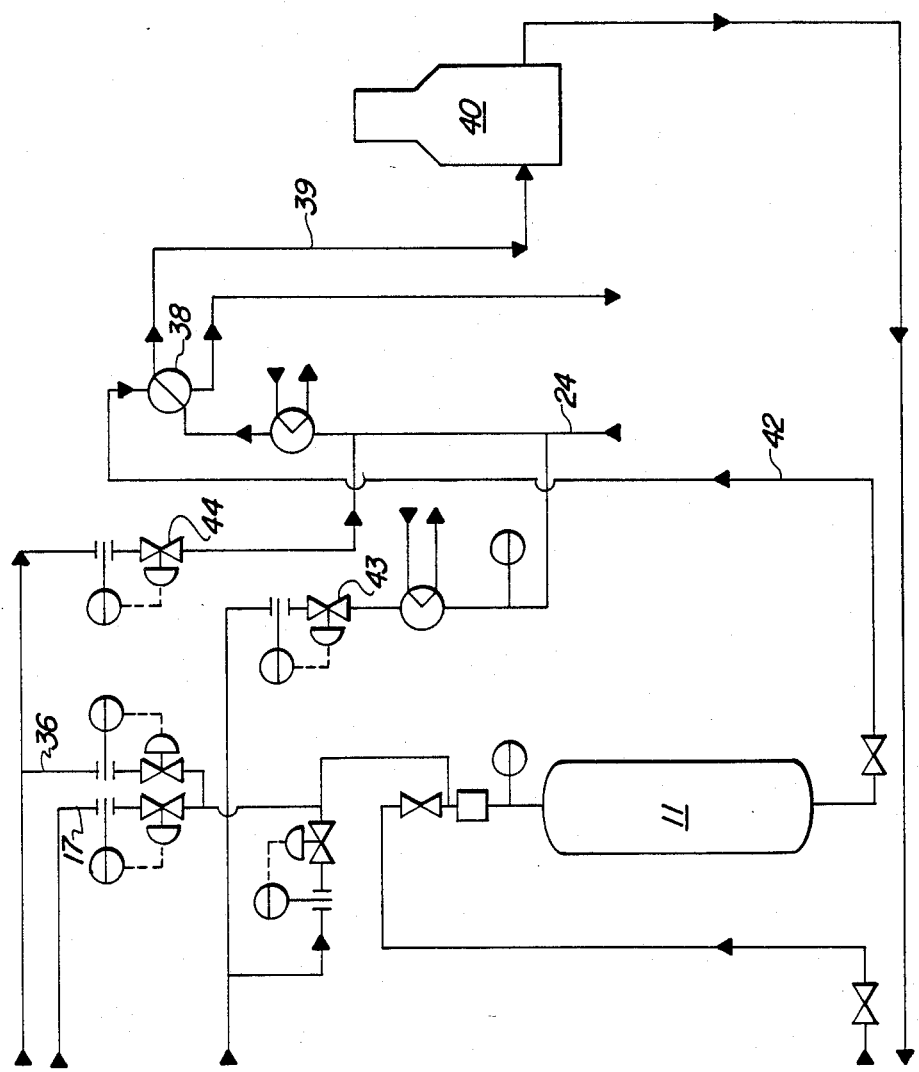

The quench arrangement of this invention is applicable to any alkylation process that is accomplished in a series of reaction zones into which at least one reactant stream is between reaction zones in sufficient liquid volume to quench the reactant stream entering the downstream reactor. In order to derive the fullest benefit from this invention, the series of reaction zones should be arranged such that each of the reaction zones in the series may be regenerated at different times. The periodic regeneration of different reaction zones places various reaction zones in the series in different degrees of catalyst deactivation. Variations in the degree of catalyst deactivation present the need for a wide variation in the heat capacity of the quenching medium which is fulfilled by the quenching arrangement of this invention.

Alkylation reactions that can utilize the arrangement of the present invention include those for alkylating aromatic hydrocarbons. The aromatic hydrocarbons alkylated in such reactions include benzenes and alkyl-substituted benzenes. Suitable alkylating agents include normal paraffins, alcohols, and halogen-substituted compounds that can supply the necessary alkyl group in the presence of suitable reaction conditions. This invention is particularly beneficial where the alkylating agent, used as the quench stream, is of a corrosive nature and an appropriate conditioning material must be added in sufficient concentration to protect metal surfaces of the processing equipment. This is particularly true of vapor phase methanol which, for corrosion purposes is combined with steam. Accordingly, it has been found that this quench system is particularly effective for the methylation of toluene with methanol in a series of reaction zones containing a catalyst and maintained at operating conditions for the selective production of para-xylene. Additional details related to the operation and arrangement of alkylation reaction systems are well known to those skilled in the art and may be obtained from the previously cited background information.

For the purposes of further explanation, this invention will be explained in the general context of a process for the methylation of toluene. The description of this invention in the limited context of a single alkylation reaction system is not meant to restrict the use of the invention or the scope of the claims set forth hereinafter to the details disclosed herein. In addition, the drawing has been simplified to include only those valves and control devices that are necessary for an understanding of this invention.

Referring again to the drawing, methanol, toluene, and steam are the primary inputs to the reaction zones. Methanol enters this preferred arrangement of this invention through line 1. As methanol enters the process, it is at ambient temperature and a pressure in the range of 50-150 psig. The methanol stream is split between header lines 2 and pipeline 3. Line 2 acts as a header for supplying cold methanol to the series of reaction zones and receives approximately 30 to 50% of the methanol feed. Methanol taken by line 3 passes into heater 4 where it is heated to a temperature in the range of 700°-850° F. (370°-455° C.) and more preferably to a range of 750°-850° F. (400°-455° C.). Header line 5 serves as a header for supplying vapor phase methanol from the heater to the various reaction zones. A side stream of steam taken from line 26 by line 27 is combined with liquid methanol in line 3 so that vapor phase methanol leaving the heater will have a minimum concentration of steam. Steam in a concentration of between 0.8 to 1.2 and preferably 0.9 to 1.1 moles of steam to moles of methanol is provided in the vapor phase methanol stream in order to keep the metal surfaces of line 5 in an oxidized state and thereby inhibit corrosion of the metal surfaces that come in contact with the hot methanol vapor. Typically, the steam supply is 150 lbs. saturated steam. Flow control devices 29 and 31, comprising a flow recorder and control valve, maintain the steam and methanol, respectively, in the desired proportions. The continuation of line 26 acts as a header for supplying steam that is combined with the methanol feed to each reaction zone. Toluene feed enters the process through line 24 where it is combined with liquid methanol regulated through a flow control device 43 and steam regulated by flow control device 44. The toluene feed stream enters the process at ambient temperature and a pressure of between ambient and 100 psig and will usually consist of relatively pure toluene having only trace amounts of paraffins.

The concentration of methanol in the feed to each reactor can be kept at a constant value equal to about 2 to 5 mol % of the feed components or the relative proportions of methanol and toluene can vary for each reaction zone. Where the relative proportion of toluene and methanol are varied between reaction zones, the concentration of methanol is kept purposefully low so that essentially all of the methanol is reacted and each reaction zone has an essentially methanol free effluent. As catalyst deactivation increases in any given reaction zone, the concentration of toluene is reduced to prevent the emergence of methanol in the effluent.

The remainder of this description will consider the case where the concentration of methanol to each reaction zone is kept constant. In such cases, the methanol concentration of the feed will usually be high enough to produce an exit methanol concentration in the effluent. The exit methanol concentration for any given reactor will vary with that reactor's degree of catalyst deactivation. Looking first at the reaction zone of reactor 6 when the catalyst in this reaction zone is fresh or newly regenerated, the exit concentration of methanol will usually be in a range of from 0.4 to 0.6 mol %. Before entering reactor 6, toluene and methanol in the desired proportion are indirectly heat exchanged with the product stream line 42 in heat exchanger 38 and then passed on to feed heater 40. Feed heater 40 heats the feed components to the desired reaction temperature for reactor 6 which is typically in a range of from 750°–1110° F. (400°–600° C.). Passage of the feed components through heater 40 will vaporize both the toluene and methanol components. For this reason, steam is added, for corrosion purposes, by line 26 in an amount to maintain the hereinbefore described ratio of methanol to steam. Additional steam in excess of that required for the methanol to steam ratio may be added as a diluent for purposes of depressing the boiling point of the feed mixture. The heated feed components flow from heater 40 to reactor 6 via line 46.

As the alkylation reaction proceeds reactor 6, or any of the reaction zones, the catalyst gradually becomes deactivated primarily by the deposition of coke but also through other reversible and non-reversible reactions with the support. As the catalyst becomes deactivated, less methanol is alkylated with the toluene, therefore, the exit methanol concentration may increase to as high as 2.0 mol % before the catalyst in any given reaction zone is regenerated.

Reactor zone 6 as well as the other reaction zones will contain a solid alkylation catalyst. This catalyst is normally a crystalline aluminosilicate zeolite. U.S. Pat. Nos. 3,965,208, 4,100,215, and 4,127,616 teach the utility of such compositions in the alkylation of aromatic hydrocarbons and in particular the methylation of toluene. A particularly preferred catalyst for the methylation of toluene with methanol to selectively obtain para-xylene is a crystalline silica composition which may contain one or more promoters such as arsenic oxide, phosphorous oxide, magnesium oxide, boron oxide, ammonium oxide, amorphous silica, and mixtures thereof. Additional details of this preferred catalyst may be obtained from U.S. Pat. No. 4,444,989.

The methylation of toluene can be carried out in an effective manner by contacting the toluene and methylating agent with a catalyst of the type described above. The reaction is carried out at temperatures ranging from about 750° F. (400° C.) to about 1110° F. (600° C.) and more preferably from about 840° F. (450° C.) to about 980° F. (525° C.). Pressure conditions within the reaction zone can vary widely between atmospheric to about 100 psia with pressures in the range of from about 25 psia to about 65 psia being preferred. The molar ratio of toluene to methylating agent in the feed can vary from 1:1 to about 1:50. Preferred ratios for operation are in the range of 3:1 to about 20:1 with ratios of 5 to about 15:1 being particularly preferred. The minimum ratio of 1:1 parts toluene to methanol is set to avoid undesirable by-products from forming in the reaction zone. The higher ratio of 50:1 is set to avoid excessive energy cost in the separation of products from any unreacted toluene feed. Useful weight hourly space velocities for the process can vary from between 1 to 500. The more common space velocity range is between 2 and 250 with about 3 to 100 being particularly preferred. As the toluene component of the feed passes serially through the reaction zones, it is progressively converted to product. As a result, for reaction purposes, the highest absolute volume of toluene will pass through reactor 6 with each succeeding reaction zone in the series receiving a lesser volume of toluene.

When exit methanol concentration exceeds a predetermined limit indicating that the catalyst in a particular reaction zone needs regeneration, the reaction zone is isolated from the system for regeneration purposes. Regeneration is primarily a coke burning operation which removes carbonaceous deposits from the catalyst and restores a significant degree of catalyst activity.

Looking then at the progress of the feed components through reactors 6–11, a pipeline 50 carries the effluent of reactor 6 to reactor 7. The contents of line 50 comprises toluene, a small amount of methanol, para-xylene product, and steam.

Branch line 12 provides additional methanol reactant for conversion in reactor 7. The contents of line 50 including the added methanol pass through a static mixer 52 which assures uniform mixing of the various feed components. The temperature and composition of the mixed component streams are obtained by on-line sensors 54 and 56, respectively. Sensor 54 consists of a simple temperature probe and sensor 56 is preferably an on-line gas chromatograph. Data from sensor 54 and 56 is used to compute interactive signals for the addition of methanol and steam. The temperature of the components in line 54 will be used to control the proportional opening of a control device 58 for the addition of vapor phase methanol and a control device 60 for the addition of liquid phase methanol from line 18. The proportion of methanol addition from control device 60 versus control device 58 will increase as sensor 54 detects an increased temperature for the reactants entering reactor 7. As gas chromatograph (GC) detects the need for an increase or decrease to concentration of methanol, the control devices 60 and 58 will be indexed to more open or more closed position in the proportion already determined for maintaining the temperature of the combined reactant stream entering reactor 7. As additional liquid methanol is added by line 18, some or all of the added methanol may become vaporized before it reaches line 50. In order to maintain the previously described concentration of methanol to steam for corrosion purposes, a control device 62 allows the regulated passage of additional steam into line 12 to compensate for the vaporization of the liquid methanol entering by line 18. Again, the entering reactants are proportioned, and the reaction zone 7 is operated such that most of the methanol is consumed in the formation of product and a stream having an increased concentration of product to toluene relative to line 50 leaves the reactor through line 64. By adding steam to line 32 in response to the addition of liquid methanol through line 18, the initial steam concentration in the vapor phase methanol stream can be kept at a minimum thereby reducing the total amount of steam that ends up in the product stream.

Toluene and product enter reaction zone 8. The addition of steam and methanol is carried out in the same manner as previously described for reaction zone 7 with a GC sensor 66 and a temperature sensor 68 being used to regulate the addition of steam and methanol through analogous control devices 70, 72, and 74 which regulate fluid passage through lines 19, 13, and 33, respectively.

Toluene and product continue to pass serially through reactors 9, 10, and 11 which are also provided with control devices and sensors of the same arrangement and type as that described for reactor 7 and 8. As methanol continues to be added to each reaction zone, the total volume of toluene continues to decrease.

The alkylation product, in this case para-xylene, steam, and any unreacted toluene and methanol are recovered by line 42 from the outlet of reactor 11. After passage through exchanger 38, the reaction zone effluent stream from line 42 enters appropriate separation facilities for the recovery of product, the production of a toluene recycle stream, the recovery of methanol, and the removal of water.

As previously mentioned, the methanol requirements for a reaction zone vary with the degree of catalyst deactivation in the previous reactor. When the effluent from a reaction zone having a high degree of deactivation enters one of the final reactors in the series of reaction zones, such as reactor 10 or 11, the quench requirements for that effluent will be very low. In such cases, essentially all of the methanol entering that reaction zone will be vapor phase. In addition, the vapor will need to be relatively hot in order to allow the combined stream of reactants to have the proper operating temperature. For this reason, the vapor methanol stream must be heated through to a relatively high temperature in reactor 4.

EXAMPLE

The following example, which is based on engineering calculations and the operation of commercial alkylation units, demonstrates the operation of a process for the methylation of toluene in accordance with this invention. Toluene is methylated for the selective production of para-xylene. In this example 33,104 lbs per hour of methanol enters the alkylation process at ambient temperature and at a pressure of 106 psig and is split into a first liquid phase stream and a second vapor stream having a temperature of 820° F. (440° C.). Five-thousand six-hundred fifteen lbs per hour of the liquid phase stream is combined with 55,302 lbs/hr of toluene and 38,415 lbs/hr of 150 lb saturated steam to form a reactor feed stream. The reactor feed stream is heated to a temperature of 925° F. (495° C.) and enters the first reaction zone at a pressure of 65 psig. The first reaction zone is one in a series of 7 reaction zones. All of the reaction zones contain approximately 34,000 lbs of a zeolitic type catalyst.

The composition and properties of the effluent from the first reaction zone is given in the table. The effluent stream passes serially through the remaining reaction zones in the series. Between each reaction zone, methanol in vapor and/or liquid phase and 150 lb saturated steam are added to each reaction zone. The Table sets forth the quantities of methanol and steam that are combined with the effluent from each reaction zone and the composition and properties of the effluent from each reaction zone both before and after the addition of steam or methanol.

|  | REACTOR EFFLUENT | | | | | | |
|---|---|---|---|---|---|---|---|
|  | 1 | 2 | 3 | 4 | 5 | 6 | 7 |
| REACTION ZONE | | | | | | | |
| WATER, LB/HR | 41,032 | 46,487 | 52,033 | 57,618 | 63,131 | 68,549 | 73,912 |
| TOLUENE, LB/HR | 256,487 | 247,523 | 238,998 | 230,763 | 222,893 | 215,118 | 207,341 |
| PARA-XYLENE LB/HR | 10,455 | 19,934 | 28,736 | 37,039 | 44,794 | 52,304 | 59,687 |
| MEOH, LB/HR | 911 | 1,112 | 1,443 | 1,791 | 2,288 | 2,673 | 3,101 |
| ORTHO & META-XYLENES, LB/HR | 308 | 720 | 1,211 | 1,771 | 2,376 | 3,036 | 3,744 |
| OTHER, LB/HR | 17,242 | 18,462 | 19,869 | 21,413 | 23,046 | 24,762 | 26,526 |
| TEMP., °F. | 937 | 938 | 941 | 927 | 929 | 932 | 935 |
| PRESS., PSIG | 61 | 56 | 52 | 48 | 43 | 39 | 35 |
| ALKYLATE AND QUENCH ADDITION | | | | | | | |
| STEAM, LB/HR | 2,808 | 2,898 | 2,917 | 2,927 | 2,848 | 2,832 | — |
| METHANOL, LB/HR | 4,995 | 5,154 | 5,188 | 5,206 | 5,066 | 5,037 | — |
| QUENCH TEMP. OF | 263 | 256 | 245 | 738 | 613 | 447 | — |
| EFFLUENT TEMP. | 923 | 923 | 923 | 923 | 923 | 923 | — |

| -continued |
| REACTOR EFFLUENT |

| | 1 | 2 | 3 | 4 | 5 | 6 | 7 |
|---|---|---|---|---|---|---|---|
| AFTER QUENCHING | | | | | | | |

As the data in the Table indicates, the upstream addition of liquid methanol provided sufficient cooling in all cases to keep the inlet temperature of each reaction zone at 920° F. (495° C.). These temperatures are within the previously mentioned desired range for the alkylation operation. Therefore, the quench system of this invention will provide the necessary cooling for an aromatic alkylation process.

I claim:

1. In a process for alkylating aromatic hydrocarbons by contacting an aliphatic alkylating agent and an aromatic hydrocarbon in a series of exothermic reaction zones where said aromatic hydrocarbon passes serially through said reaction zones, a separate stream of said alkylating agent enters the inlet of each reaction zone, the aromatic hydrocarbon, and alkylation agent contact an alkylation catalyst at alkylation conditions in each reaction zone, an alkylation product passes serially from the first reaction zone in said series to the last reaction zone and an alkylate product is recovered from the last reaction zone in said series, the improvement wherein: at least one of said separate streams of alkylating agent that enters the inlet of each reaction zone is a quench stream comprising vapor phase alkylation agent and liquid phase alkylation agent, and the relative proportion of liquid and vapor phase alkylating agent in said quench stream is controlled to provide a predetermined degree of quenching for the reaction zones located downstream of the inlet where said quench stream enters the process.

2. The process of claim 1 wherein a liquid phase alkylating agent is divided into first and second fractions, said second fraction is heated to provide a vapor phase alkylating agent and each of the separate streams of alkylating agent are composed of a portion of at least one of said first and second fractions.

3. The process of claim 1 wherein the combined vapor phase and liquid phase alkylating agent are passed through a mixing device before entering a reaction zone.

4. The process of claim 2 wherein the stream of alkylating agent entering a reaction zone inlet that is intermediate any two reaction zones is combined with said aromatic stream ahead of said inlet, the temperature of the combined aromatic and alkylation stream is measured ahead of said inlet, the measured value is compared with a predetermined temperature value, and the relative proportion of liquid to vapor phase alkylating agent is adjusted upward when said measured temperature exceeds said predetermined temperature and downward when said predetermined temperature exceeds said measured temperature.

5. In a process for methylating toluene by contacting a methylating agent and toluene with a solid alkylation catalyst in a series of exothermic reaction zones where a toluene feed stream passes serially through said reaction zones, a separate stream of methylating agent and steam enter the inlet of each reaction zone, the reaction product of toluene and the methylating agent passes from each reaction zone to any succeeding reaction zones and a product comprising xylenes is recovered from the last reaction zone in said series, the improvement wherein the methylating agent is divided into first and second fractions said second fraction is heated to provide a vapor phase methylating agent, each of said separate methylating streams is composed of a portion of at least one of said fractions, the stream of alkylating agent entering a reaction zone inlet that is intermediate any two reaction zones is combined with said toluene feed stream ahead of said inlet at a first mixing point to form a combined feed, the temperature of the combined feed is measured ahead of said inlet, the measured temperature value is compared with a predetermined temperature value, and the relative proportion of liquid phase to vapor phase methylating agent is adjusted upward when said measured temperature exceeds said predetermined temperature and downward when said predetermined temperature exceeds said measured temperature.

6. The process of claim 5 wherein the combined streams of toluene and methylating agent are passed through a mixing device and said temperature is measured downstream of said mixing device.

7. The process of claim 5 wherein said methylating agent is methanol.

8. The process of claim 7 wherein the vapor phase fraction of said methylating agent contains at least 0.8 moles of steam for each mole of methanol.

9. The process of claim 1 wherein said reaction zones contain a catalyst comprising a crystalline aluminosilicate zeolite.

10. The process of claim 9 wherein said methylating agent is methanol and each stream entering any of said reaction zones contains between 0.8 and 1.2 moles of steam for each mole of methanol.

11. The process of claim 5 wherein said second fraction is combined, prior to heating, with a first quantity of steam in a predetermined molar concentration of methylating agent and steam, liquid phase methylating agent is combined with vapor phase methylating agent at a second mixing point, located downstream of said first mixing point, and a second quantity of steam is added to said vapor phase methylating agent at a point ahead of said second mixing point in an amount sufficient to maintain said predetermined molar concentration of steam and vapor phase methylating after vaporization of said liquid phase methylating agents.

12. The process of claim 11 wherein said methylating agent is methanol and said predetermined molar ratio is from 0.8 to 1.2 moles of steam to mole of methanol.

13. The process of claim 12 wherein said vapor phase stream is heated to a temperature of from 750° F. (400° C.) to 850° F. (455° C.) and said predetermined molar ratio is from 0.90 to 1.1 moles of steam to moles of methanol.

* * * * *